US007016035B2

(12) United States Patent
Wu et al.

(10) Patent No.: US 7,016,035 B2
(45) Date of Patent: Mar. 21, 2006

(54) FIBER OPTICAL APPARATUS AND SYSTEM FOR IN SITU LASER PLASMA SPECTROSCOPY

(75) Inventors: Pingfan Wu, Niskayuna, NY (US); Pamela Benicewicz, N. Loudonville, NY (US); Elena Rozier, Schenectady, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 10/605,371

(22) Filed: Sep. 25, 2003

(65) Prior Publication Data

US 2005/0068524 A1   Mar. 31, 2005

(51) Int. Cl.
*G01J 3/443* (2006.01)
*G01N 21/63* (2006.01)

(52) U.S. Cl. ........................................... 356/318
(58) Field of Classification Search .............. 356/316, 356/318
See application file for complete search history.

(56) References Cited

U.S. PATENT DOCUMENTS

| 4,645,342 | A | 2/1987 | Tanimoto et al. ........... 356/318 |
| 5,446,538 | A | 8/1995 | Noll ........................... 356/318 |
| 5,798,832 | A | 8/1998 | Hnilica et al. .............. 356/316 |
| 6,008,896 | A | 12/1999 | Sabsabi et al. ............. 356/318 |
| 6,762,835 | B1 * | 7/2004 | Zhang et al. ............... 356/318 |
| 6,762,836 | B1 * | 7/2004 | Benicewicz et al. ........ 356/318 |

OTHER PUBLICATIONS

Rai et al., "Parametric Study of Fiber-Optic Laser-Induced Breakdown Spectroscopy Probe for Analysis of Aluminum Alloys", Spectrochimica Acta Part B, vol. 56, Issue 12, Dec. 10, 2001, pp. 2371-2383.*

* cited by examiner

*Primary Examiner*—F. L. Evans
(74) *Attorney, Agent, or Firm*—Fletcher Yoder

(57) ABSTRACT

In in-situ laser plasma spectroscopy (LPS) apparatus includes an enclosure for housing a laser energy source and associated signal coupling optics. A main fiber is attached to the enclosure at a first end of the main fiber, and attached to a probe at a second end of the main fiber. The main fiber is configured for transmitting input laser energy from the laser energy source to a target and for transmitting laser induced plasma emission signals back from the target. The probe has a single focal lens for directing the input laser energy from the main fiber to the target, and for directing the laser induced plasma emission signals from the target to the main fiber.

42 Claims, 5 Drawing Sheets

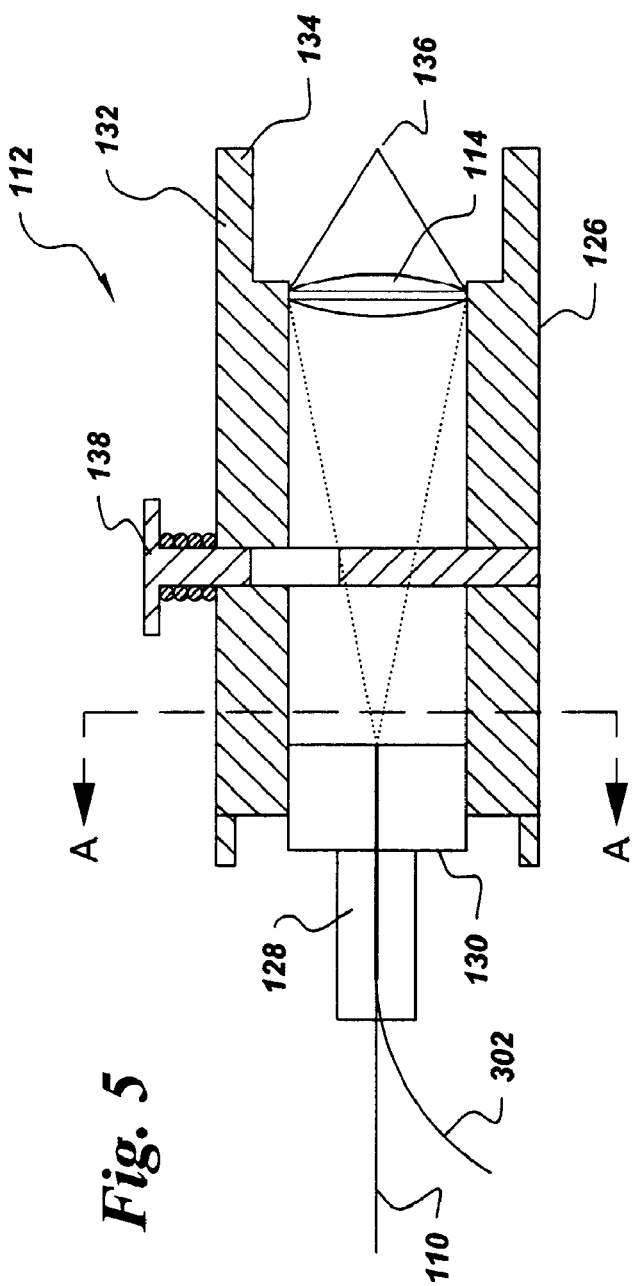
*Fig. 5*
*Fig. 7*
*Fig. 6*

FIBER OPTICAL APPARATUS AND SYSTEM FOR IN SITU LASER PLASMA SPECTROSCOPY

BACKGROUND OF THE INVENTION

The present disclosure relates generally to laser emission spectroscopy and, more particularly, to an apparatus and system for in situ laser plasma spectroscopy analysis.

The elemental composition of solids can be determined rapidly and simply with the use of laser plasma spectroscopy (LPS). Also known as laser induced breakdown spectroscopy (LIBS) and laser-induced plasma spectroscopy (LIPS) (as well as other names), LPS uses a high peak power laser pulse to form a microplasma or spark on a sample to be analyzed. A small amount of the sample material is vaporized and a plasma is formed, with the emitting species (e.g., ions, atoms and molecules) in the plasma being identified by spectrally and temporally resolving the plasma light.

Although LPS measurements may be performed remotely by pointing the laser beam directly on the sample in free space, it is an undesirable technique to be used by people working in the field. In an alternative method of remote LPS spectroscopy analysis, the laser output is coupled to an optical fiber that transmits the laser energy to a generally inaccessible location. A probe or borescope then directs the laser energy to the sample surface. In this type of apparatus, a beam splitter is typically inserted inside the probe to separate the incident laser beam from the returning LPS signal, which is in turn coupled to a fiber optic connected to a spectrometer.

Conventional probe designs utilize at least two fibers inside the probe package itself, one for the laser delivery and the other one for LPS signal collection. However, this type of design makes the probe bulky, which can be unsuitable in certain field applications. In other probe designs, two fibers are bundled together as a pair. Laser energy exiting from the laser delivering fiber is focused on the surface of the sample by optics that are also used to image the plasma radiation generated on the sample surface back to the laser delivering fiber. Since the plasma has finite dimension and the optics have aberrations associated therewith, the image of the plasma on the side of fiber is extended, and thus the second fiber next to the laser delivering fiber also collects some LPS generated radiation. However, the collection is secondary and the efficiency is therefore low. Alternatively, other approaches have utilized a curved mirror on the side of the laser-focusing lens to reflect the plasma radiation to a collecting chamber. Again, these types of systems that feature multiple optical devices within the probe assembly itself are very bulky.

Accordingly, it would be desirable to be able to have a field suitable, portable LPS system that can be moved from location to location and can also withstand a harsh environment, featuring (among other aspects) a compact probe that can be held by hand, inserted into and directed by a guide tube, or carried by a robot to a desired location.

BRIEF DESCRIPTION OF THE INVENTION

The above discussed and other drawbacks and deficiencies of the prior art are overcome or alleviated by an in-situ laser plasma spectroscopy (LPS) apparatus. In an exemplary embodiment, the apparatus includes an enclosure for housing a laser energy source. A main fiber is connected to the enclosure at a first end of the main fiber, and connected to a probe at a second end of the main fiber. The main fiber is configured for transmitting input laser energy from the laser energy source to a target and for transmitting laser induced plasma emission signals back from the target. The probe has a single focal lens for directing the input laser energy from the main fiber to the target, and for directing the laser induced plasma emission signals from the target to the main fiber.

In another aspect, an in-situ laser plasma spectroscopy (LPS) apparatus includes an enclosure for housing a laser energy source. A main fiber is connected to the enclosure at a first end of the main fiber, and connected to a probe at a second end of the main fiber. The main fiber is configured for transmitting input laser energy from the laser energy source to a target and for transmitting laser induced plasma emission signals back from the target. The probe has a single focal lens for directing the input laser energy from the main fiber to the target, and for directing the laser induced plasma emission signals from the target to the main fiber. At least one satellite fiber is connected to the probe, the at least one satellite fiber configured so as to transmit a portion of laser induced plasma emission signals back from said target.

In still another aspect, an in-situ laser plasma spectroscopy (LPS) system, includes an enclosure for housing a laser energy source. A main fiber is connected to the enclosure at a first end of the main fiber, and connected to a probe at a second end of the main fiber. The main fiber is configured for transmitting input laser energy from said laser energy source to a target and for transmitting laser induced plasma emission signals back from said target. The probe has a single focal lens for directing the input laser energy from the main fiber to the target, and for directing the laser induced plasma emission signals from the target to the main fiber. A beam splitter is disposed within said enclosure, the beam splitter configured for directing the input laser energy from the laser energy source into the main fiber, the beam splitter further configured for directing the laser induced plasma emission signals from the main fiber to a second fiber connected to the enclosure. The system further includes a spectrometer device connected to the second fiber, the spectrometer device configured to receive the laser induced plasma emission signals for analysis of the laser induced plasma emission signals. An intensified charge-coupled device (ICCD) camera is attached to the spectrometer device, and a computer is in communication with the ICCD camera.

BRIEF DESCRIPTION OF THE DRAWINGS

Referring to the exemplary drawings wherein like elements are numbered alike in the several Figures:

FIGS. 5–7 are cross sectional views illustrating various embodiments of satellite fiber configurations.

DETAILED DESCRIPTION OF THE INVENTION

Disclosed herein is portable apparatus system that provides in situ and remote elemental analysis of a material surface. Elemental composition identification is based on the laser plasma spectroscopy (LPS) technique, wherein a probe includes a main fiber for delivering both the laser pulse and returning LPS signal. In an alternative embodiment, additional satellite fibers are bundled inside the probe together with the main laser/LPS signal delivering fiber, for transmitting the LPS signal to other devices (e.g., a sensitive photodiode to monitor the LPS signal fluctuation, and a PMT which controls a shutter to block the laser once the spectrum of a substrate material is detected). On the other side of the main fiber, a beam splitter separates the laser and the LPS signal. The LPS signal is then imaged to another fiber, which is connected to the entrance of the spectrometer. In addition, the laser and all the fiber coupling optics are sealed in a single enclosed chamber, so that the apparatus can withstand harsh field environment conditions. This configuration also renders the system as a Class I laser.

Figure 1:
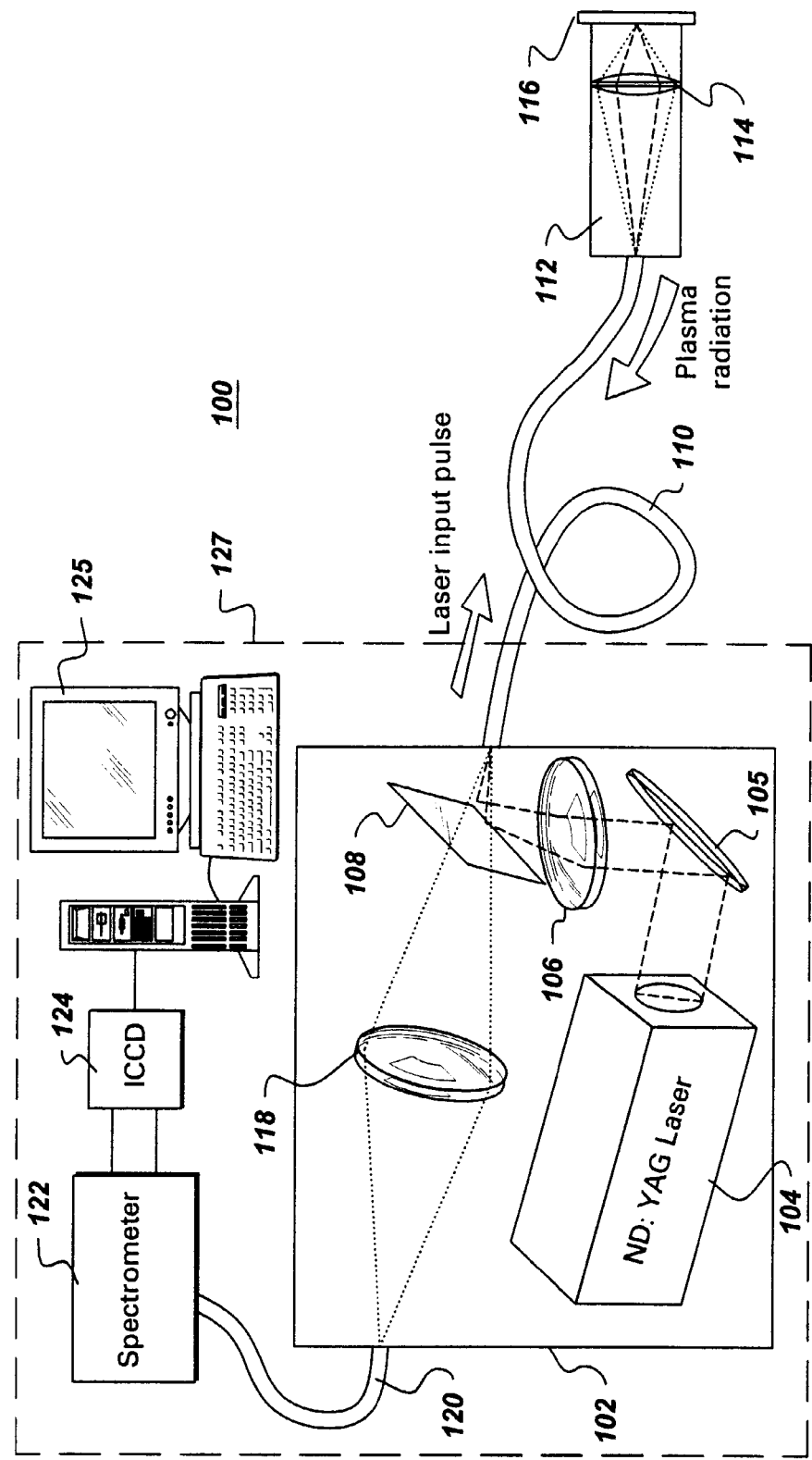
FIG. 1 is a schematic drawing of an in situ, laser plasma spectroscopy (LPS) system, in accordance with an embodiment of the invention.

Referring initially to FIG. 1, there is shown a schematic diagram of an in situ, laser plasma spectroscopy (LPS) system 100, in accordance with an embodiment of the invention. A sealed enclosure 102 includes a Q-switched, sealed Nd:YAG laser 104 operating at a wavelength of 1064 nm, which generates laser pulses reflected by a mirror 105 and focused by a first lens 106. The generated pulses are then reflected by a short-wavelength pass/long-wavelength reflect beam splitter 108 before being coupled into a first (main) fiber 110. The main fiber 110, which has a relatively large core diameter (e.g., larger than 0.6 millimeters), is connected at one end thereof to the enclosure 102 using an SMA or other kind of suitable optical connector (not shown in FIG. 1). At the opposite end thereof, the main fiber 110 connects to a probe 112.

As the laser pulses exit from the main fiber 110 within the probe 112, they are focused by an uncoated, small, short focal length lens 114. The focal lens 114 has an exemplary diameter of about 12 millimeters (mm) and an exemplary focal length of about 12 mm. In addition to focusing the incident laser pulses on the target 116 to be analyzed, the lens 114 also images the resulting laser-induced breakdown plasma emission back to the surface of the laser delivering fiber (i.e., the main fiber 110). Accordingly, the main fiber 110 also serves the purpose of transmitting the plasma emission signal back to the entrance surface thereof at sealed enclosure 102, wherein the short-wavelength pass/long-wavelength reflect beam splitter 108 separates the 1064-nm laser pulses from the shorter wavelength LPS signals.

Enclosure 102 includes a second lens 118 for imaging the LPS signals to the entrance surface of a second fiber 120, the second lens 118 has exemplary dimensions of about 50.8 mm in diameter and about 100 mm in focal length. It will be noted that lens 118 is disposed within enclosure 102 such that it is equidistant between the main fiber 110 and the second fiber 120. Thus, there is a one to one imaging from the main fiber laser entrance surface to the second fiber LPS signal entrance surface. In other words, the main and second fibers may have the same core size. Moreover, the second fiber 120 is designed such that the numerical aperture (NA) entering therein is the same as the NA designed for a spectrometer 122 to which the other end of second fiber 120 is connected.

Although the second fiber 120 may be a single large core fiber, it could also be a fiber bundle in which the small individual fibers thereof are arranged in a circular configuration on the enclosure side and realigned in a linear configuration on the spectrometer entrance side. Accordingly, the spectrometer 122 includes a fiber adaptor (not shown) for the fiber containing the incoming LPS signal. The incoming LPS signal is then dispersed and imaged on an ICCD (intensified charge-coupled device) camera 124. The resulting image of the ICCD camera 124 is transferred to a computer 125 for elemental analysis.

In one embodiment, the components of the system 100 (except for the probe 112 and main fiber 110 are enclosed and transported in a vibration-damped case 127, as schematically depicted by the dashed line in FIG. 1. The case 127 may include casters to enhance mobility of the system 100. During transportation, the main fiber 110 may be disconnected from both the probe 112 and the enclosure 102.

Figure 2:
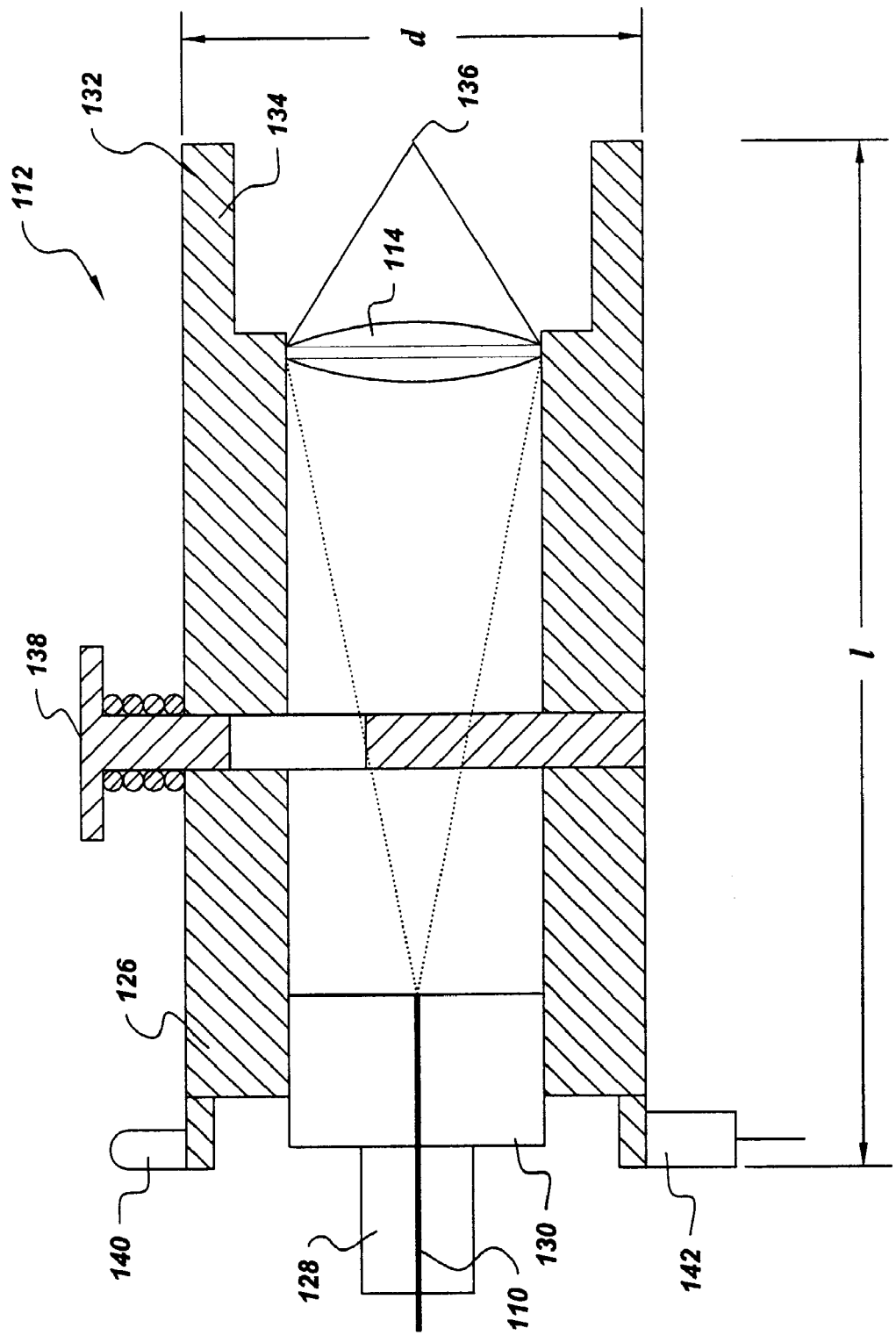
FIG. 2 is a cross sectional view of a probe included within the LPS system of FIG. 1.

FIG. 2 is a cross sectional view of one possible embodiment of the design of the probe 112. In the embodiment depicted, the probe includes a generally cylindrical housing 126 having a suitably compact length, l, and diameter, d, so as to comfortably fit in the palm of a user's hand. As is shown, the probe 112 has just the single uncoated lens 114 for directing laser pulses from the main fiber 110 to the target surface. The main fiber 110 is shown encased in a protective sheath 128 (e.g., stainless steel) and enters the housing 126 through an optical connector 130, such as an SMA connector.

The probe 112 further includes a stop 132 such that the end 134 thereof coincides with the focal point 136 of the laser pulse exiting the lens 114. In field applications, a user may therefore position the probe 112 in direct contact with the sample surface without regard to the position of the laser focal point. Again, the lens 114 also images the resulting plasma radiation from the sample surface back to the main fiber 110. A mechanically depressible shutter 138 is further provided so that the user can selectively unblock the emergence of the laser energy from the probe. In addition, the housing 126 may also include an indicator 140 (e.g., an LED) for indicating to the user whenever laser 104 power is on. If such an indicator 140 is implemented, a power lead 142 is used to provide power thereto.

Figure 3:
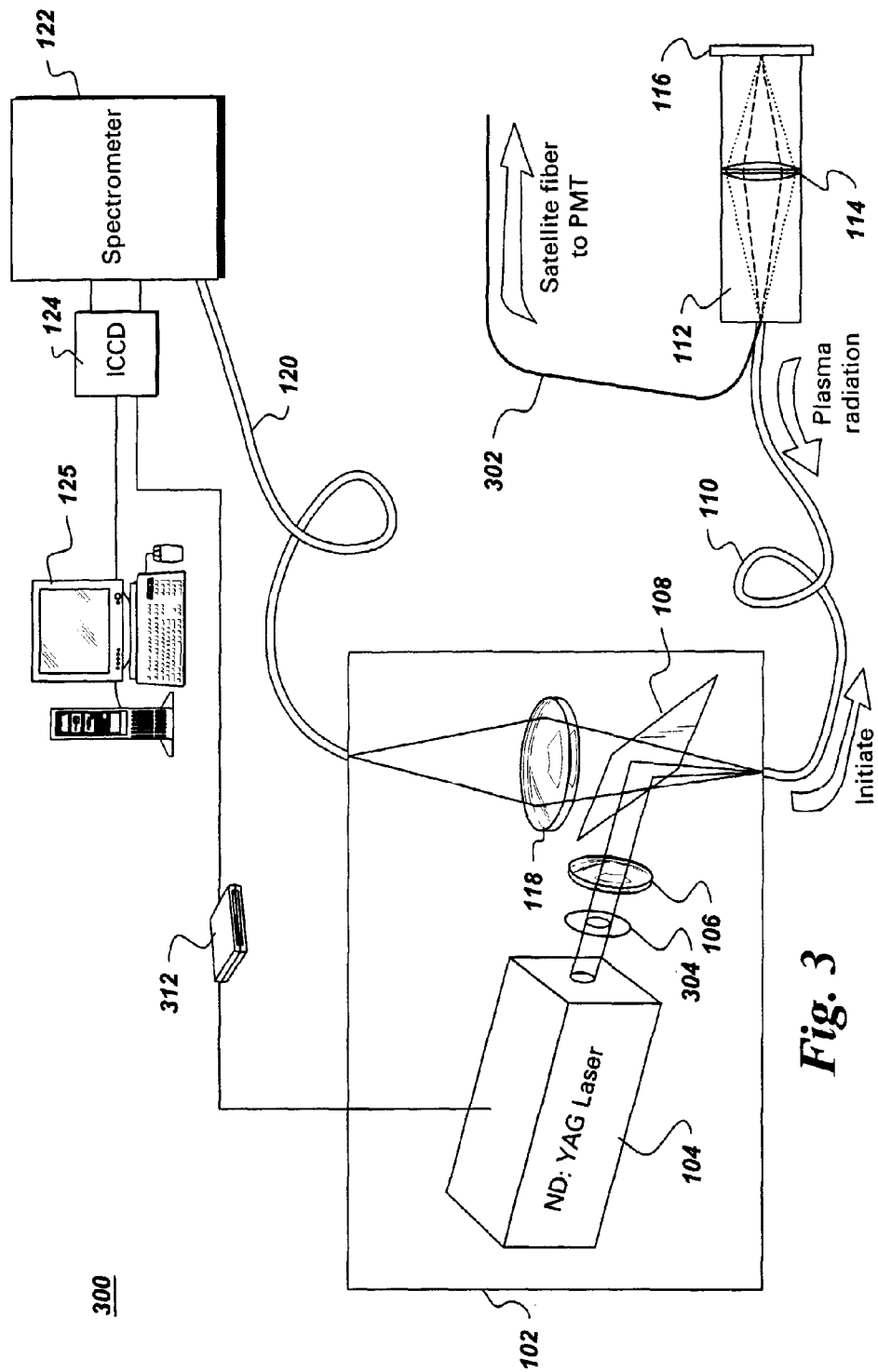
FIG. 3 is a schematic drawing of an alternative embodiment of the LPS system of FIG. 1.

Referring now to FIG. 3, there is shown a schematic drawing of an alternative embodiment of an LPS system 300. For purposes of clarity, like elements in FIG. 3 with respect to FIG. 1 are designated with like reference numerals. In addition to the features previously discussed, LPS system 300 further includes a satellite (i.e., second) fiber 302 coupled to the main fiber 110 proximate to the input of probe 112. The satellite fiber 302 carries a portion of the LPS radiation signals to be transmitted to another monitoring device(s), depending on the desired application(s) thereof.

Figure 4:
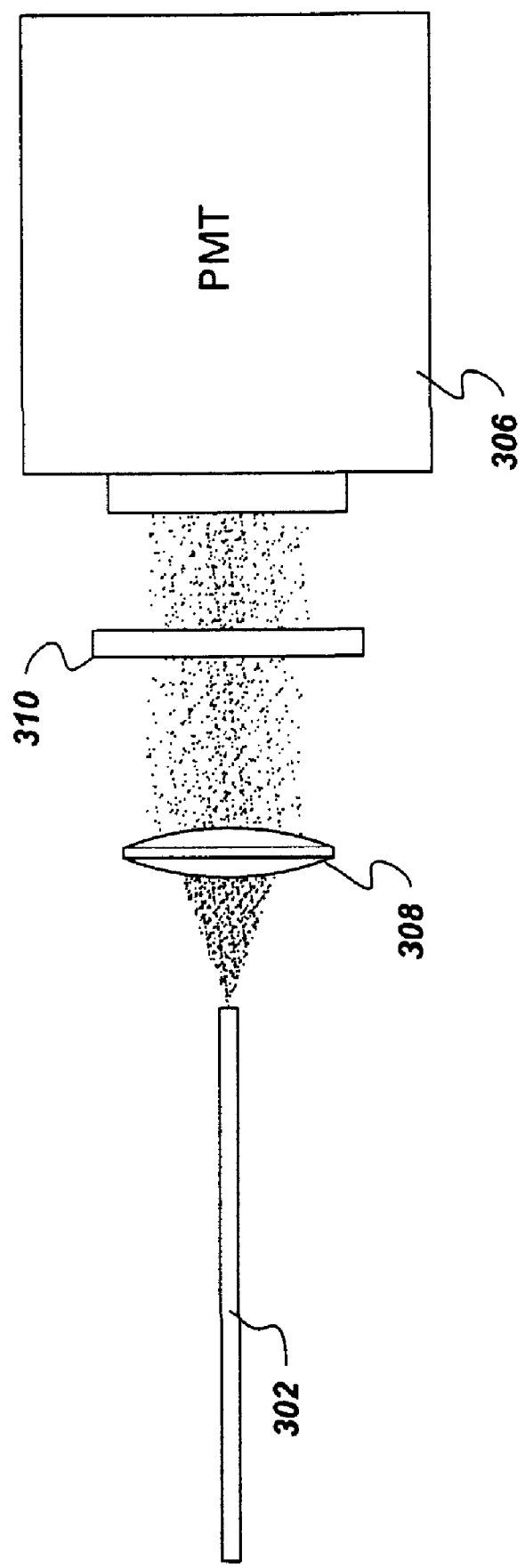
FIG. 4 is a schematic drawing of a satellite fiber and PMT detector used in conjunction with the embodiment of FIG. 3.

For example, in the embodiment depicted, the satellite fiber 302 may be used in conjunction with a shuttering system in order to protect certain material present in the target 116, wherein upon detection of the presence of ablated protected material, an appropriate control signal is used to engage a shutter 304 located adjacent the output of laser 104 in enclosure 102. The shuttering system may be a photomultiplier tube (PMT) based system, in which the LPS radiation collected by the satellite fiber 302 is transmitted to a PMT detector 306, as shown in more detail in FIG. 4. In particular, the LPS radiation from the satellite fiber 302 is collimated by a lens 308 and blocked by a narrow band pass filter 310. The narrow band pass filter 310, which may be an interference filter or other type of filter, is configured so as to transmit a narrow range of wavelengths characteristic of the target material sought to be protected from laser damage. Once the LPS signal passes through the filter 310, and the PMT output thereafter exceeds a preset threshold, a timing box 312 (FIG. 3) will send a signal to the shutter 304 to block the laser output.

It will be appreciated that in the satellite fiber embodiment of FIG. 3, the LPS signal collected therefrom may also be delivered to a photodiode in order to monitor the intensity of the LPS signal fluctuation itself. In other words, the LPS signal collected by the satellite fiber 302 may be used as part of a diagnostic operation. If the LPS signal intensity is too low, this could indicate, for example, that (1) the main laser delivering fiber may be broken; or (2) that there is an issue with probe alignment, in that the sample is not at the focusing point of the probe. Additionally, the secondary LPS signal can be used in data analysis to normalize the main LPS signal to correct for changes in the signal that are due to fluctuations in the laser energy.

Finally, FIGS. 5 through 7 illustrates various possible configurations for the satellite fiber 302 layouts with respect to the main fiber 110. In FIG. 5, the satellite fiber(s) 302 is packed along with the main fiber 110 within the connector 130 of the probe 112 such that the returning LPS signals are collected on both the satellite fiber 302 and the main fiber. When viewed along the line A—A in FIG. 5, the satellite fiber(s) may be arranged linearly along the main fiber 110, as shown in FIG. 6. Alternatively, multiple satellite fibers 302 may be arranged hexagonally around the main fiber for efficient packing, as shown in FIG. 7.

In one embodiment, the main fiber 110 and satellite fiber 302 have both a core and cladding, and may be placed precisely on a grooved wafer. The main and satellite fibers may also be bundled together with high temperature epoxy filling the empty space therebetween. Alternatively, the main fiber and satellite fiber can have just a core, along with high refraction index material to bundle them together. In FIG. 5, the plasma emission on the sample surface at point 136 is imaged to the surface of the main fiber 110 by lens 114. However, since the lens 114 has aberrations and since the plasma is moving away from the sample surface, the plasma image on the fiber surface is much larger in area than the core surface area of main fiber 110. Thus, the plasma emission image is also directed to the satellite fiber 302.

An exemplary LPS system in accordance with the above described embodiment of FIG. 1 was constructed. In the exemplary system, both the main fiber 110 and second fiber 120 both have a 1 mm core diameter. Forty (40) mJ pulses were coupled to the probe 112, which focused the input laser spot to a spot size of about 0.5 mm in diameter. The repetition rate of the input laser pulse was varied from about 1 to about 10 Hz. Both zinc and silicon were used as target samples, and strong LPS signals were obtained therefrom. Furthermore a PMT detector in accordance with the embodiment of FIG. 3 was also successfully tested.

As will be appreciated, the configuration of the above described system embodiments provide for a compact fiber optics system for in situ laser plasma spectroscopy detection. The LPS system is characterized by a compact probe with a single uncoated lens having a small diameter and short focal length. A single main fiber may therefore be used to deliver both the laser pulse and the returning LPS signal. The main fiber has a sufficiently large core diameter, so that the plasma radiation from the sample surface may be easily imaged back to the main fiber inside the probe. Optionally, one or more satellite (secondary) fibers may be bundled together with the main fiber inside the probe. The satellite fiber(s) collects a portion of LPS signal and carries it to other devices. The probe further includes a stop to fix the laser focal point imaged by the single lens inside the probe.

A sealed enclosure is used to house both the laser and the remaining optics for withstanding harsh environments and for rendering the system as a Class I laser. The enclosure features fiber connectors (such as SMA or similar types) so that other components in the LPS system can be easily assembled to the package through fiber connections. In addition to withstanding harsh environmental conditions, the system components excluding the probe (i.e., the enclosed laser chamber, laser power supply, spectrometer, ICCD camera, ICCD controller and computer) are placed and fixed tightly in another enclosed case that has vibration damping. For ease of transportation, wheels may be provided underneath the case.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

The invention claimed is:

1. An in-situ laser plasma spectroscopy (LPS) apparatus, comprising:
   an enclosure for housing a laser energy source;
   a main fiber connected to said enclosure at a first end of said main fiber, and connected to a probe at a second end of said main fiber, said main fiber configured for transmitting input laser energy from said laser energy source to a target and for transmitting laser induced plasma emission signals back from said target; and
   said probe being moveable with respect to said target and having a single focal lens, said input laser energy from said main fiber being focused to said target by movement of said probe for directing said laser induced plasma emission signals from said target to said main fiber.

2. The LPS apparatus of claim 1, wherein said enclosure further includes a beam splitter for directing said input laser energy from said laser energy source into said main fiber, said beam splitter further configured for directing said laser induced plasma emission signals from said main fiber to a second fiber in communication with said enclosure, wherein said second fiber is configured to transmit said laser induced plasma emission signals to a spectrometer device for analysis of said laser induced plasma emission signals.

3. The LPS apparatus of claim 2, wherein said enclosure further includes:
   a first lens for focusing said input laser energy reflected from said beam splitter into said main fiber; and
   a second lens for focusing said laser induced plasma emission signals directed from said beam splitter into said second fiber.

4. The LPS apparatus of claim 3, wherein said second lens is positioned equidistant between said main fiber and said second fiber.

5. The LPS apparatus of claim 4, wherein said second lens has a focal length of about 100 millimeters.

6. The LPS apparatus of claim 2, wherein said beam splitter further comprises one of a short wavelength pass filter and a band-reflection filter.

7. The LPS apparatus of claim 1, wherein said enclosure comprises a sealed enclosure.

8. The LPS apparatus of claim 1, wherein said probe further comprises a stop at one end thereof, said stop configured such that an exit end of said probe corresponds to a focal point of said single focal lens.

9. The LPS apparatus of claim 8, wherein said single focal lens has a focal length of about 12 millimeters.

10. The LPS apparatus of claim 8, wherein said probe further comprises a depressible shutter for manually unblocking the emergence of input laser energy from said probe.

11. The LPS apparatus of claim 8, wherein said probe further comprises an indicator for indicating said laser energy source is turned on.

12. An in-situ laser plasma spectroscopy (LPS) apparatus, comprising:
   an enclosure for housing a laser energy source;
   a main fiber connected to said enclosure at a first end of said main fiber, and connected to a probe at a second end of said main fiber, said main fiber configured for transmitting input laser energy from said laser energy source to a target and for transmitting laser induced plasma emission signals back from said target;
   said probe having a single focal lens for directing said input laser energy from said main fiber to said target, and for directing said laser induced plasma emission signals from said target to said main fiber; and
   at least one satellite fiber attached within said probe, said at least one satellite fiber configured so as to transmit a portion of laser induced plasma emission signals back from said target.

13. The LPS apparatus of claim 12, wherein said enclosure further includes a beam splitter for directing said input laser energy from said laser energy source into said main fiber, said beam splitter further configured for directing said laser induced plasma emission signals from said main fiber to a second fiber connected to said enclosure, wherein said second fiber is configured to transmit said laser induced plasma emission signals to a spectrometer device for analysis of said laser induced plasma emission signals.

14. The LPS apparatus of claim 13, wherein said enclosure further includes:
   a first lens for focusing said input laser energy reflected from said beam splitter into said main fiber; and
   a second lens for focusing said laser induced plasma emission signals directed from said beam splitter into said second fiber.

15. The LPS apparatus of claim 14, wherein said second lens is positioned equidistant between said main fiber and said second fiber.

16. The LPS apparatus of claim 15, wherein said second lens has a focal length of about 100 millimeters.

17. The LPS apparatus of claim 13, wherein said beam splitter further comprises one of a short wavelength pass filter and a band-reflection filter.

18. The LPS apparatus of claim 12, wherein said enclosure comprises a sealed enclosure.

19. The LPS apparatus of claim 12, wherein said probe further comprises a stop at one end thereof, said stop configured such that an exit end of said probe corresponds to a focal point of said single focal lens.

20. The LPS apparatus of claim 19, wherein said single focal lens has a focal length of about 12 millimeters.

21. The LPS apparatus of claim 19, wherein said probe further comprises a depressible shutter for manually unblocking the emergence of input laser energy from said probe.

22. The LPS apparatus of claim 19, wherein said probe further comprises an indicator for indicating said laser energy source is turned on.

23. The LPS apparatus of claim 19, wherein said probe further comprises a connector, said connector configured to maintain said at least one satellite fiber and said main fiber in a linear arrangement.

24. The LPS apparatus of claim 19, wherein said probe further comprises a connector, said connector configured to maintain said at least one satellite fiber and said main fiber in a hexagonal arrangement.

25. An in-situ laser plasma spectroscopy (LPS) system, comprising:
   an enclosure for housing a laser energy source;
   a main fiber connected to said enclosure at a first end of said main fiber, and connected to a probe at a second end of said main fiber, said main fiber configured for transmitting input laser energy from said laser energy source to a target and for transmitting laser induced plasma emission signals back from said target;
   said probe being moveable with respect to said target and having a single focal lens, said input laser energy from said main fiber being focused to said target by movement of said probe for directing said laser induced plasma emission signals from said target to said main fiber;
   a beam splitter disposed within said enclosure, said beam splitter configured for directing said input laser energy from said laser energy source into said main fiber, said beam splitter further configured for directing said laser induced plasma emission signals from said main fiber to a second fiber connected to said enclosure;
   a spectrometer device attached to said second fiber, said spectrometer device configured to receive said laser induced plasma emission signals for analysis of said laser induced plasma emission signals;
   an intensified charge-coupled device (ICCD) camera attached to said spectrometer device; and
   a computer in communication with said ICCD camera.

26. The LPS system of claim 25, wherein said enclosure further includes:
   a first lens for focusing said input laser energy reflected from said beam splitter into said main fiber; and
   a second lens for focusing said laser induced plasma emission signals directed from said beam splitter into said second fiber.

27. The LPS system of claim 26, wherein said second lens is positioned equidistant between said main fiber and said second fiber.

28. The LPS system of claim 27, wherein said second lens has a focal length of about 100 millimeters.

29. The LPS system of claim 25, wherein said beam splitter further comprises one of a short wavelength pass filter and a band-reflection filter.

30. The LPS system of claim 25, wherein said enclosure comprises a sealed enclosure.

31. The LPS system of claim 25, wherein said probe further comprises a stop at one end thereof, said stop configured such that an exit end of said probe corresponds to a focal point of said single focal lens.

32. The LPS system of claim 31, wherein said single focal lens has a focal length of about 12 millimeters.

33. The LPS system of claim 31, wherein said probe further comprises a depressible shutter for manually unblocking the emergence of input laser energy from said probe.

34. The LPS system of claim 31, wherein said probe further comprises an indicator for indicating said laser energy source is turned on.

35. The LPS system of claim 25, wherein said main fiber is removably connectable to said enclosure and said probe, and said second fiber is removably connectable to said enclosure and said spectrometer through an associated fiber connector.

36. The LPS system of claim 25, wherein said second fiber has a same core size as said main fiber.

37. The LPS system of claim 25, wherein said second fiber further comprises a fiber bundle having a plurality of individual fibers, wherein said individual fibers are arranged in a circular configuration at the connection to said enclosure and arranged in a linear configuration at the connection to said spectrometer.

38. The LPS system of claim 25, further comprising at least one satellite fiber in communication with said probe, said at least one satellite fiber configured so as to transmit a portion of laser induced plasma emission signals back from said target.

39. The LPS system of claim 38, further comprising a shuttering system for blocking said input laser energy from said target upon detection of detection of one or more selected wavelengths from said laser induced plasma emission signals.

40. The LPS system of claim 39, wherein said shuttering system further comprises:

a photomultiplier tube (PMT) detector for receiving a portion of laser induced plasma emission signals; and a shutter disposed within said enclosure;

wherein said PMT detector is configured to engage said shutter closed upon detecting a threshold level of said one ore more selected wavelengths from said laser induced plasma emission signals.

41. The LPS system of claim 40, wherein said shuttering system further comprises:

a collimating lens for receiving said laser induced plasma emission signals from said satellite fiber; and a narrow band pass filter for receiving collimated plasma emission signals from said collimating lens.

42. The LPS system of claim 25, wherein said enclosure for housing said laser energy source, said second fiber, said spectrometer device, said ICCD camera and said computer are enclosed within a transportable, vibration damped case.

* * * * *